US012793211B2

(12) United States Patent
Hattori et al.

(10) Patent No.: US 12,793,211 B2
(45) Date of Patent: Nov. 10, 2026

(54) MEDICAL IMAGE PROCESSING APPARATUS, MEDICAL IMAGE PROCESSING METHOD, AND STORAGE MEDIUM

(71) Applicant: Canon Kabushiki Kaisha, Tokyo (JP)

(72) Inventors: Chihiro Hattori, Nasushiobara (JP); Yasuko Fujisawa, Nasushiobara (JP)

(73) Assignee: Canon Kabushiki Kaisha, Tokyo (JP)

( * ) Notice: Subject to any disclaimer, the term of this patent is extended or adjusted under 35 U.S.C. 154(b) by 401 days.

(21) Appl. No.: 18/303,047

(22) Filed: Apr. 19, 2023

(65) Prior Publication Data

US 2023/0360209 A1 Nov. 9, 2023

(30) Foreign Application Priority Data

May 9, 2022 (JP) ................................ 2022-077065

(51) Int. Cl.
*G06T 7/00* (2017.01)
*A61B 6/00* (2024.01)

(52) U.S. Cl.
CPC .............. *G06T 7/0012* (2013.01); *A61B 6/52* (2013.01); *G06T 2207/10072* (2013.01)

(58) Field of Classification Search
None
See application file for complete search history.

(56) References Cited

U.S. PATENT DOCUMENTS

| | | | | |
|---|---|---|---|---|
| 11,922,629 B2 * | 3/2024 | Guida | G01R 33/5608 |
| 2015/0262388 A1 | 9/2015 | Ishii et al. | |
| 2021/0056690 A1 * | 2/2021 | Futamura | G16H 30/40 |
| 2022/0012874 A1 * | 1/2022 | Maier-Hein | G06T 7/254 |
| 2022/0076422 A1 * | 3/2022 | Guida | G01R 33/5608 |
| 2022/0415013 A1 * | 12/2022 | Yoo | A61B 6/5217 |
| 2023/0041098 A1 * | 2/2023 | Rao | G10L 21/0208 |
| 2023/0298178 A1 * | 9/2023 | Notoshi | G16H 30/20 382/132 |

FOREIGN PATENT DOCUMENTS

| | | |
|---|---|---|
| JP | 2019-115680 A | 7/2019 |
| JP | 2020-124435 A | 8/2020 |

OTHER PUBLICATIONS

CN110570491; human-assisted machine translation of the Chinese patent application with figures translated; Xing et al Sep. 6, 2019 (Year: 2019).*

* cited by examiner

*Primary Examiner* — Nancy Bitar
(74) *Attorney, Agent, or Firm* — Oblon, McClelland, Maier & Neustadt, L.L.P.

(57) ABSTRACT

A medical image processing apparatus of an embodiment includes processing circuitry. The processing circuitry acquires a medical image and a heat map. The processing circuitry determines a transmittance of the heat map on the basis of pixel values of the medical image. The processing circuitry generates a superimposed image obtained by superimposing the heat map having the determined transmittance on the medical image.

12 Claims, 7 Drawing Sheets

MEDICAL IMAGE PROCESSING APPARATUS, MEDICAL IMAGE PROCESSING METHOD, AND STORAGE MEDIUM

CROSS-REFERENCE TO RELATED APPLICATION

The present application claims priority based on Japanese Patent Application No. 2022-077065, filed May 9, 2022, the content of which is incorporated herein by reference.

FIELD

Embodiments disclosed in this specification and drawings relate to a medical image processing apparatus, a medical image processing method, and a storage medium.

BACKGROUND

Software that displays a heat map superimposed on a grayscale image such as a computed tomography (CT) image is generally well-known. Such a heat map can vary in transmittance (transparency), and when the transmittance is increased, it is possible to view the heat map while allowing a base CT image to be viewed.

As a conventional technique, a method of changing a transmittance depending on values of a heat map value is known. This is a method in which a user adjusts a transmittance on a user interface in particular. In addition, there is also a method of automatically determining colors for the purpose of improving the visibility of a heat map. However, at the time of automatically determining the transmittance of a heat map, a uniform transmittance is applied to the entire image in many cases. Since the transmittance of the heat map does not depend on map values or distribution and the same transmittance is used for an entire image, there is a problem that it is difficult to see a base CT image or the heat map in some cases.

DETAILED DESCRIPTION

A medical image processing apparatus, a medical image processing method, and a storage medium according to embodiments will be described below with reference to the drawings. A medical image processing apparatus according to an embodiment includes processing circuitry. The processing circuitry acquires a medical image and a heat map. The processing circuitry determines a transmittance of the heat map on the basis of pixel values of the medical image. The processing circuitry generates a superimposed image which is an image in which the heat map having the determined transmittance is superimposed on the medical image. This makes it possible to improve visibility of the medical image and the heat map.

[Configuration of Medical Image Processing Apparatus]

Figure 1:
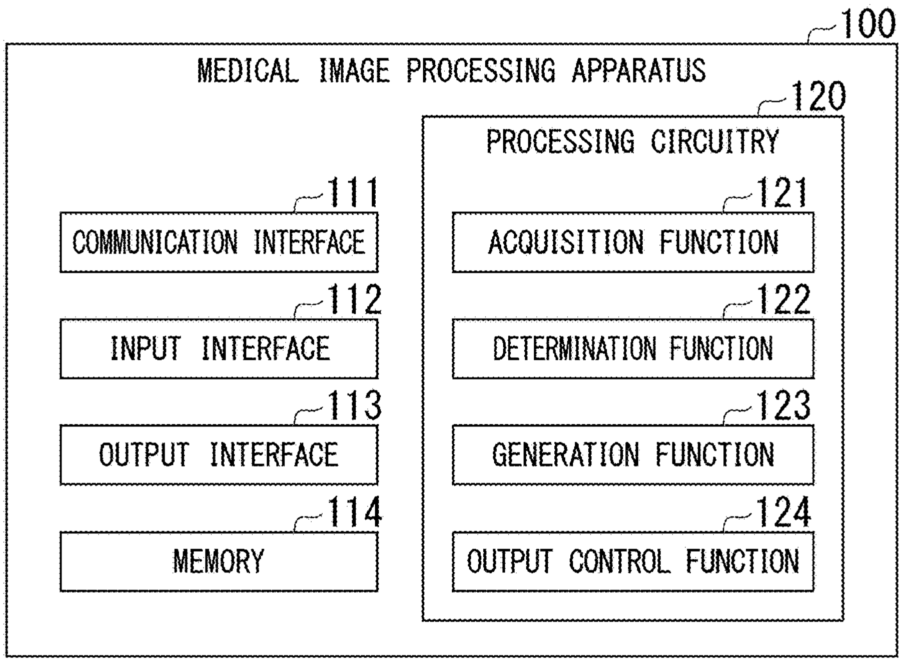
FIG. 1 is a diagram showing a configuration example of a medical image processing apparatus in an embodiment.

FIG. 1 is a diagram showing a configuration example of a medical image processing apparatus 100 in an embodiment. The medical image processing apparatus 100 includes, for example, a communication interface 111, an input interface 112, an output interface 113, a memory 114, and processing circuitry 120.

The medical image processing apparatus 100 may be a single apparatus or may be a system in which a plurality of apparatuses connected via a communication network NW operate in cooperation. That is, the medical image processing apparatus 100 may be realized by a plurality of computers (processors) included in a distributed computing system or a cloud computing system.

The communication interface 111 communicates with a medical image diagnostic apparatus or the like via a communication network NW. The communication interface 111 includes, for example, a network interface card (NIC), an antenna for wireless communication, and the like.

The communication network NW may mean any information communication network that uses telecommunication technology. For example, the communication network NW includes a telephone communication network, an optical fiber communication network, a cable communication network, a satellite communication network, and the like in addition to a wireless/wired local area network (LAN) such as a hospital backbone LAN and an Internet network.

Medical image diagnostic apparatuses are, for example, modalities such as an X-ray computed tomography (CT) apparatus, a magnetic resonance imaging (MRI) apparatus, and an acoustic image diagnostic apparatus.

The input interface 112 receives various input operations from an operator, converts the received input operations into electrical signals, and outputs the electrical signals to the processing circuitry 120. For example, the input interface 112 includes a mouse, a keyboard, a trackball, a switch, a button, a joystick, a touch panel, and the like. The input interface 112 may be, for example, a user interface that receives voice input, such as a microphone. When the input interface 112 is a touch panel, the input interface 112 may also have a display function of a display 113*a* included in the output interface 113, which will be described later.

The input interface 112 in this specification is not limited to one having physical operation components such as a mouse and a keyboard. For example, examples of the input interface 112 also include electrical signal processing circuitry that receives an electrical signal corresponding to an input operation from an external input device provided separately from the apparatus and outputs the electrical signal to a control circuit.

The output interface 113 includes, for example, the display 113*a* and a speaker 113*b*.

The display 113*a* displays various types of information. For example, the display 113*a* displays an image generated by the processing circuitry 120, a graphical user interface (GUI) for receiving various input operations from an operator, and the like. For example, the display 113*a* is a liquid crystal display (LCD), a cathode ray tube (CRT) display, an organic electroluminescence (EL) display, or the like. The display 113*a* is an example of a "display unit."

The speaker 113*b* outputs information input from the processing circuitry 120 as sound.

The memory 114 is realized by, for example, a semiconductor memory element such as a random access memory (RAM) or a flash memory, a hard disk, or an optical disc. These non-transitory storage media may be realized by other storage devices such as a network attached storage (NAS) and an external storage server device connected via the communication network NW. Further, the memory 114 may also include non-transitory storage media such as a read only memory (ROM) and a register.

The processing circuitry 120 includes, for example, an acquisition function 121, a determination function 122, a generation function 123, and an output control function 124. The acquisition function 121 is an example of an "acquisition unit," the determination function 122 is an example of a "determination unit," and the generation function 123 is an example of a "generation unit." The output control function 124 is an example of a "display control unit."

The processing circuitry 120 realizes these functions by a hardware processor (computer) executing a program stored in the memory 114 (storage circuit), for example.

The hardware processor in the processing circuitry 120 means, for example, a circuit (circuitry) such as a central processing unit (CPU), a graphics processing unit (GPU), an application specific integrated circuit (ASIC), a programmable logic device (for example, a simple programmable logic device (SPLD), a complex programmable logic device (CPLD), or a field programmable gate array (FPGA)). Instead of storing a program in the memory 114, the program may be incorporated directly into the circuit of the hardware processor. In this case, the hardware processor realizes the functions by reading and executing the program incorporated in the circuit. The aforementioned program may be stored in the memory 114 in advance or may be stored in a non-transitory storage medium such as a DVD or a CD-ROM and installed in the memory 114 from the non-transitory storage medium when the non-transitory storage medium is set in a drive device (not shown) of the medical image processing apparatus 100. The hardware processor is not limited to being configured as a single circuit and may be configured as one hardware processor by combining a plurality of independent circuits to implement each function. Further, a plurality of components may be integrated into one hardware processor to realize each function.

[Processing Flow of Medical Image Processing Apparatus]

Figure 2:
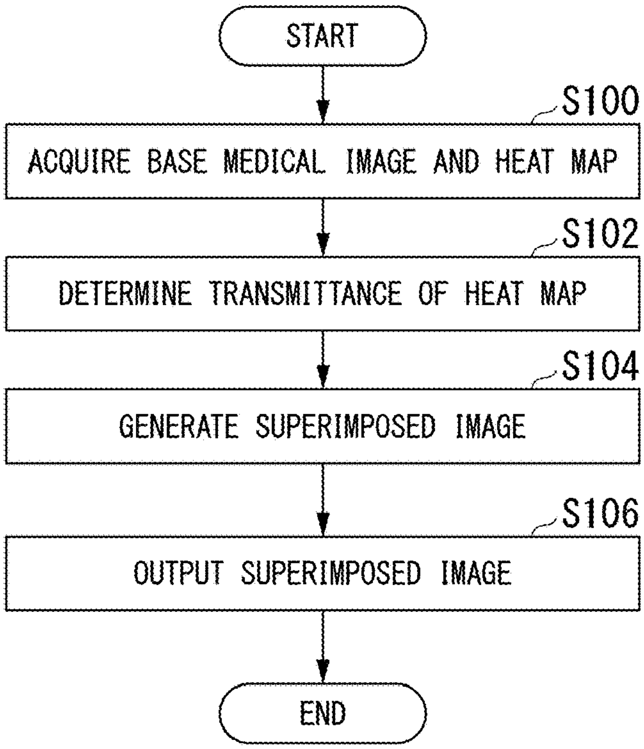
FIG. 2 is a flowchart showing a flow of a series of processing of processing circuitry in an embodiment.

A series of processing by the processing circuitry 120 of the medical image processing apparatus 100 will be described below with reference to a flowchart. FIG. 2 is a flowchart showing a series of processing of the processing circuitry 120 according to an embodiment. In this flowchart, as an example, a medical image is a CT image.

First, the acquisition function 121 acquires a CT image and a heat map from a medical image diagnostic apparatus via the communication interface 111 (step S100). The CT image may be, for example, a two-dimensional MPR image or a three-dimensional image. Further, the CT image may be a curved planar reconstruction (CPR) or straight planar reconstruction (SPR) image.

Next, the determination function 122 determines a transmittance p of the heat map on the basis of pixel values of the CT image (step S102). The transmittance may be read as transmissivity or transparency.

Next, the generation function 123 generates a superimposed image, which is an image obtained by superimposing the heat map with the transmittance p determined by the determination function 122 on the CT image (step S104).

Next, the output control function 124 outputs the superimposed image generated by the generation function 123 (step S108). For example, the output control function 124 may cause the display 113*a* of the output interface 113 to display the superimposed image or transmit the superimposed image to an external display device via the communication interface 111. Accordingly, processing of this flowchart ends.

[First Determination Method]

Figure 3:
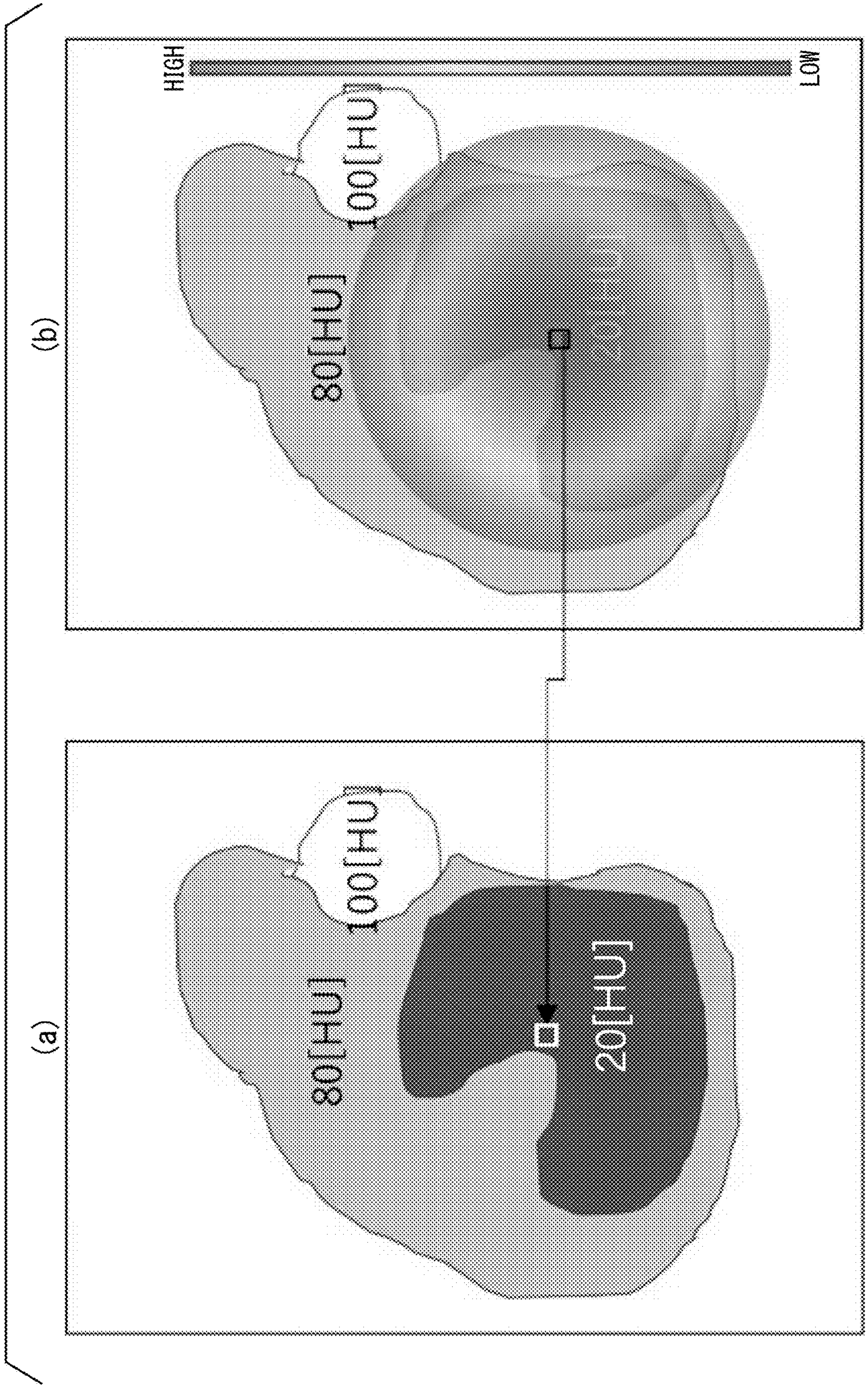
FIG. 3 is a diagram showing a CT image and a heat map side by side.

A first method for determining the transmittance p of the heat map will be described below. FIG. 3 is a diagram showing a CT image and a heat map side by side. FIG. 3(*a*) shows a CT image, and FIG. 3(*b*) shows a CT image on which a heat map is superimposed. The determination function 122 sets, as a point of interest, a pixel having the largest pixel value on the heat map. Based on a CT value of a pixel on the CT image which overlaps with the point of interest on the heat map when the heat map is superimposed on the CT image, the determination function 122 determines a weighting factor w1 for transmittance depending on the CT value.

Figure 4:
FIG. 4 is a diagram showing a state of change of a weighting factor of a transmittance according to CT values.

FIG. 4 is a diagram showing a state of change of the weighting factor w1 for transmittance according to the CT value. In the illustrated example, when the heat map is superimposed on the CT image, the CT value of the pixel on the CT image that overlaps the point of interest on the heat map is 20 [HU]. For example, 20 [HU], which is the reference, corresponds to the smallest weighting factor w1 (closest to 0), and as it becomes smaller or larger than 20 [HU], the weighting factor w1 increases (becomes closer to 1).

Next, the determination function 122 determines a weighting factor w2 for transmittance on the basis of information obtained from the heat map. The information obtained from the heat map includes, for example, the Euclidean distance from the point of interest on the heat map and other geometric information. In the following description, as an example, the information obtained from the heat map is the Euclidean distance from the point of interest on the heat map.

Figure 5:
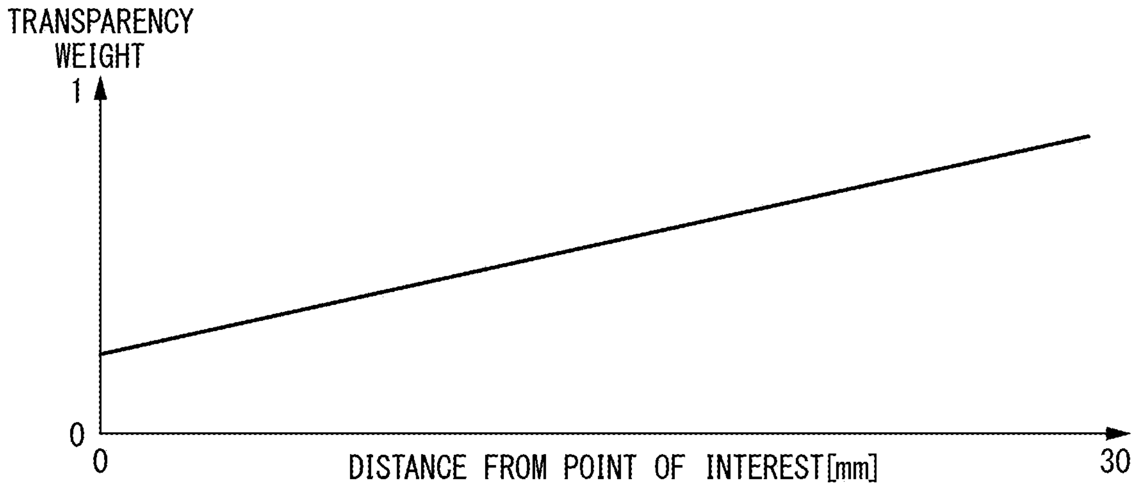
FIG. 5 is a diagram showing a state of change of the weighting factor of the transmittance according to a Euclidean distance from a point of interest.

FIG. 5 is a diagram showing a state of change of the weighting factor w2 for transmittance according to the Euclidean distance from the point of interest. As in the illustrated example, the determination function 122 may make the weighting factor w2 the smallest (make it closest to 0) at the point of interest and may increase the weighting factor w2 (make it closer to 1) as the distance from the point of interest increases.

Then, the determination function 122 determines the transmittance p [%] of each pixel in the heat map on the basis of the following formula (1).

$$p = w1 \times w2 \times 100 \quad (1)$$

As represented by formula (1), the determination function 122 determines the value obtained by multiplying the product of the weighting factor w1 and the weighting factor w2 by 100 as the transmittance p of each pixel in the heat map.

In the first determination method, the CT value that is the reference on the CT image may be a statistical value of pixel values of an area on the CT image that is superimposed on an area having pixel values equal to or greater than a threshold value on the heat map. The statistical value is, for example, a maximum value, a minimum value, an average value, a median value, or the like. Further, in the first determination method, the point of interest on the heat map may be set to the center of gravity of an area having pixel values equal to or greater than the threshold value on the heat map or may be set to the center of gravity of an area in which the CT value on the CT image is equal to or greater than the threshold value. Further, the point of interest on the heat map may be set to the center of gravity of a specific structure extracted from the CT image by image processing. Moreover, the transmittance p of each pixel in the heat map is not limited to the product of the weighting factor w1 and the weighting factor w2 and may be calculated by a non-linear function.

[Second Determination Method]

A second method for determining the transmittance of a heat map will be described below. In the second determination method, similarly to the first determination method, the determination function 122 sets, as a point of interest, a pixel having the largest pixel value on the heat map. Based on a CT value of a pixel on the CT image which overlaps with the point of interest on the heat map when the heat map is superimposed on the CT image, the determination function 122 determines the weighting factor w1 for transmittance according to the CT value.

Next, the determination function 122 determines the weighting factor w2 for transmittance on the basis of an attribute of a patient who is an imaging target at the time of generating the medical image. Attributes of a patient may include, for example, the age, sex, weight, height, place of residence, days of hospital stay, medical history, and the like of the patient. In the following description, as an example, an attribute of a patient is the age of the patient.

Figure 6:
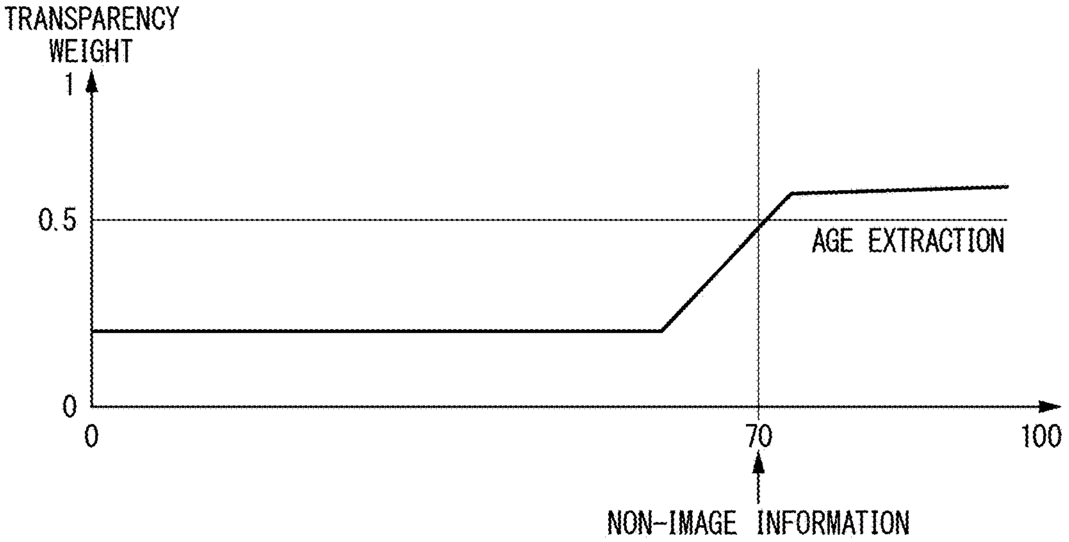
FIG. 6 is a diagram showing a state of change of the weighting factor of the transmittance according to the age of a patient.

FIG. 6 is a diagram showing a state of change of the weighting factor w2 for transmittance according to the age of the patient. As in the illustrated example, the determination function 122 may decrease the weighting factor w2 (make it closer to 0) for younger patients and increase the weighting factor w2 (make it closer to 1) for older patients. More specifically, the determination function 122 may set a certain weighting factor w2 for patients aged 0 to 60, increase the weighting factor w2 as the patient's age increases from 60 years old to 75 years old, and make the weighting factor w2 constant for patients aged 75 and over.

Then, the determination function 122 determines the value obtained by multiplying the product of the weighting factor w1 and the weighting factor w2 by 100 as the transmittance p of each pixel in the heat map, as represented by formula (1).

In general, with age, the functions of organs decline, and when a CT image is captured using a contrast agent, tissues tend to be less stained (a CT value is less likely to increase). Therefore, even in the same tissues, the CT value varies depending on age. In the second determination method, the transmittance of the heat map, in which the CT value varies due to individual differences, is corrected according to age.

In the second determination method, the weighting factor w2 depending on age need not be used to calculate the transmittance p of all pixels in the heat map. For example, the determination function 122 may use the weighting factor w2 depending on age only at the time of calculating the transmittance p of an area on the heat map superimposed on an area having the CT value equal to or greater than the threshold value on the CT image. Further, the determination function 122 may use the weighting factor w2 depending on age only at the time of calculating the transmittance p of an area on the heat map superimposed on a specific structure on the CT image. Further, the determination function 122 may determine the weighting factor w2 according to other attributes such as sex and race without being limited to the age of a patient.

[Third Determination Method]

A third method for determining the transmittance of the heat map will be described below. In the third determination method, similarly to the first and second determination methods, the determination function 122 sets, as a point of interest, a pixel having the largest pixel value on the heat map. Based on a CT value of a pixel on the CT image which overlaps with the point of interest on the heat map when the heat map is superimposed on the CT image, the determination function 122 determines the weighting factor w1 for transmittance according to the CT value.

Next, the determination function 122 determines the weighting factor w2 for transmittance on the basis of a distance from the contour of a specific structure (for example, the contour of an organ) on the CT image.

Figure 7:
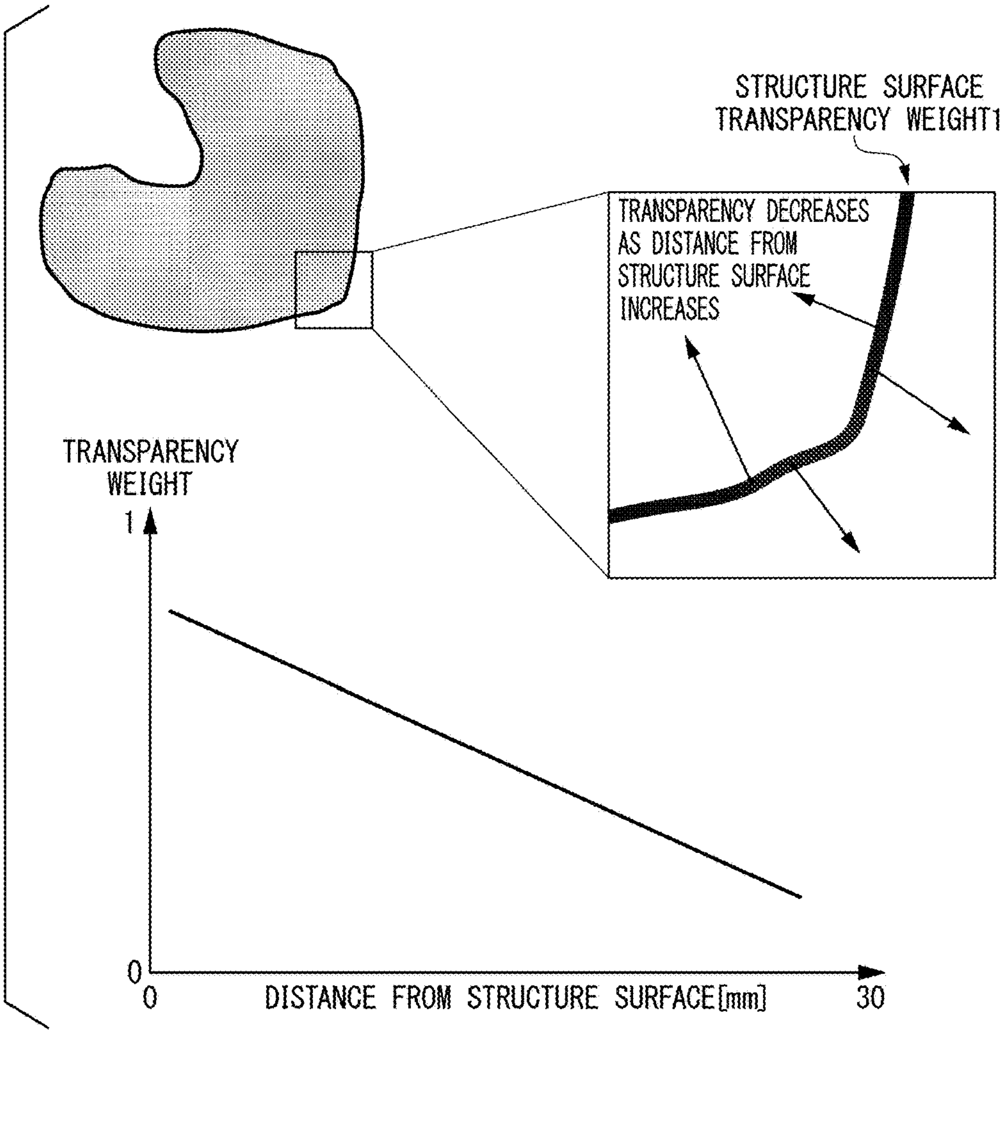
FIG. 7 is a diagram showing a state of change of the weighting factor of the transmittance according to a distance from the contour of a specific structure.

FIG. 7 is a diagram showing a state of change of the weighting factor w2 for transmittance according to the distance from the contour of a specific structure. As in the illustrated example, the determination function 122 may increase the weighting factor w2 most (make it close to 1) near the contour of the structure and decrease the weighting factor w2 (make it close to 0) as the distance from the contour of the structure increases.

Then, the determination function 122 determines the value obtained by multiplying the product of the weighting factor w1 and the weighting factor w2 by 100 as the transmittance p of each pixel in the heat map, as represented by formula (1).

In the third determination method, calculation of the weighting factor w2 according to the distance from the surface of the structure may differ between the inside of the structure and the outside of the structure. Alternatively, the weighting factor w2 may be calculated for only one of the inside and outside of the structure.

Further, if there are a plurality of structures, the determination function 122 may determine the weighting factor w2 according to the distance from the contour of each structure.

Figure 8:
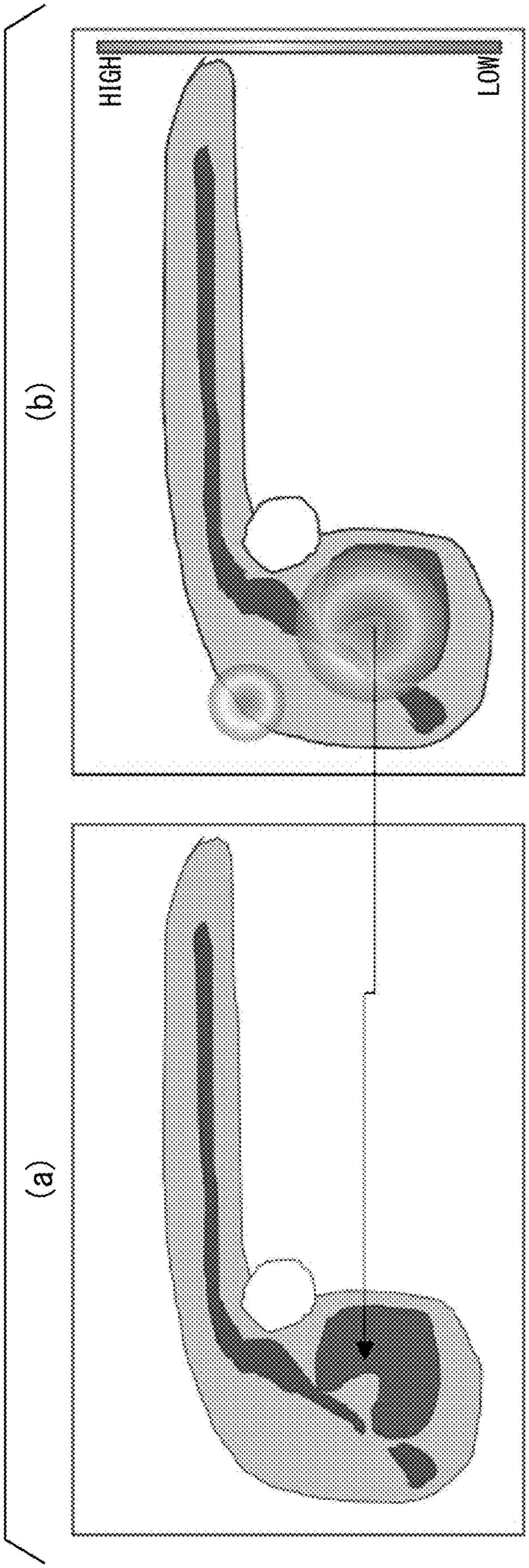
FIG. 8 is a diagram showing a CT image in which a plurality of structures are present and a heat map side by side.
Figure 9:
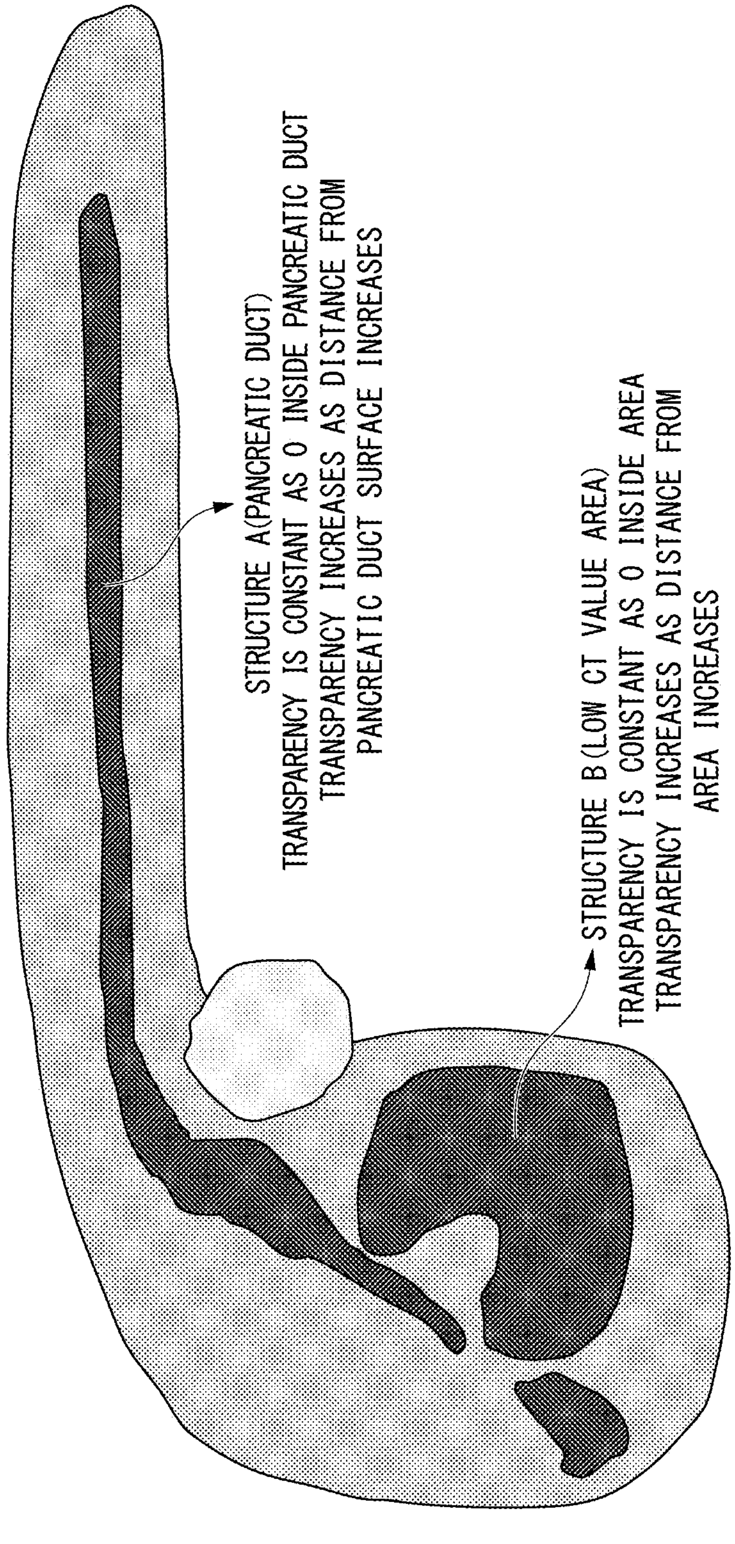
FIG. 9 is a diagram for describing a method of determining a weighting factor when a plurality of structures are present.

FIG. 8 is a diagram showing a CT image in which a plurality of structures are present and a heat map side by side. FIG. 9 is a diagram describing a method of determining the weighting factor w2 when there are a plurality of structures. As illustrated, for example, it is assumed that a structure A such as a pancreatic duct and a structure B having a CT value less than the threshold value are present on the CT image. In such a case, the determination function 122 sets the weighting factor w2 to 0 within the structure A and increases the weighting factor w2 as the distance from the structure A increases. Similarly, the determination function 122 sets the weighting factor w2 to 0 within the structure B and increases the weighting factor w2 as the distance from the structure B increases.

Then, the determination function 122 determines the transmittance p [%] of each pixel in the heat map on the basis of the following formula (2).

$$p = w1 \times w2_A \times w2_B \times 100 \quad (2)$$

For example, the determination function 122 determines the value obtained by multiplying the product of the weighting factor w1, a weighting factor $w2_A$ depending on the distance from the contour of structure A, and a weighting factor $w2_B$ depending on the distance from the contour of structure B by 100 as the transmittance p of each pixel in the heat map, as represented by formula (2). Accordingly, the transmittance p of a pixel value far from both structure A and structure B becomes greater than the transmittance p of a pixel value close to both structures or either structure (the pixel becomes transparent).

According to the embodiment described above, the processing circuitry 120 acquires a medical image and a heat map. The processing circuitry 120 determines the transmittance p of each pixel of the heat map on the basis of pixel values of the medical image. Then, the processing circuitry 120 generates a superimposed image, which is an image obtained by superimposing the heat map having the determined transmittance p on the medical image and causes the display 113*a* to display the superimposed image. This improves the visibility of the medical image, the heat maps, or superimposed images thereof.

OTHER EMBODIMENTS

Figure 10:
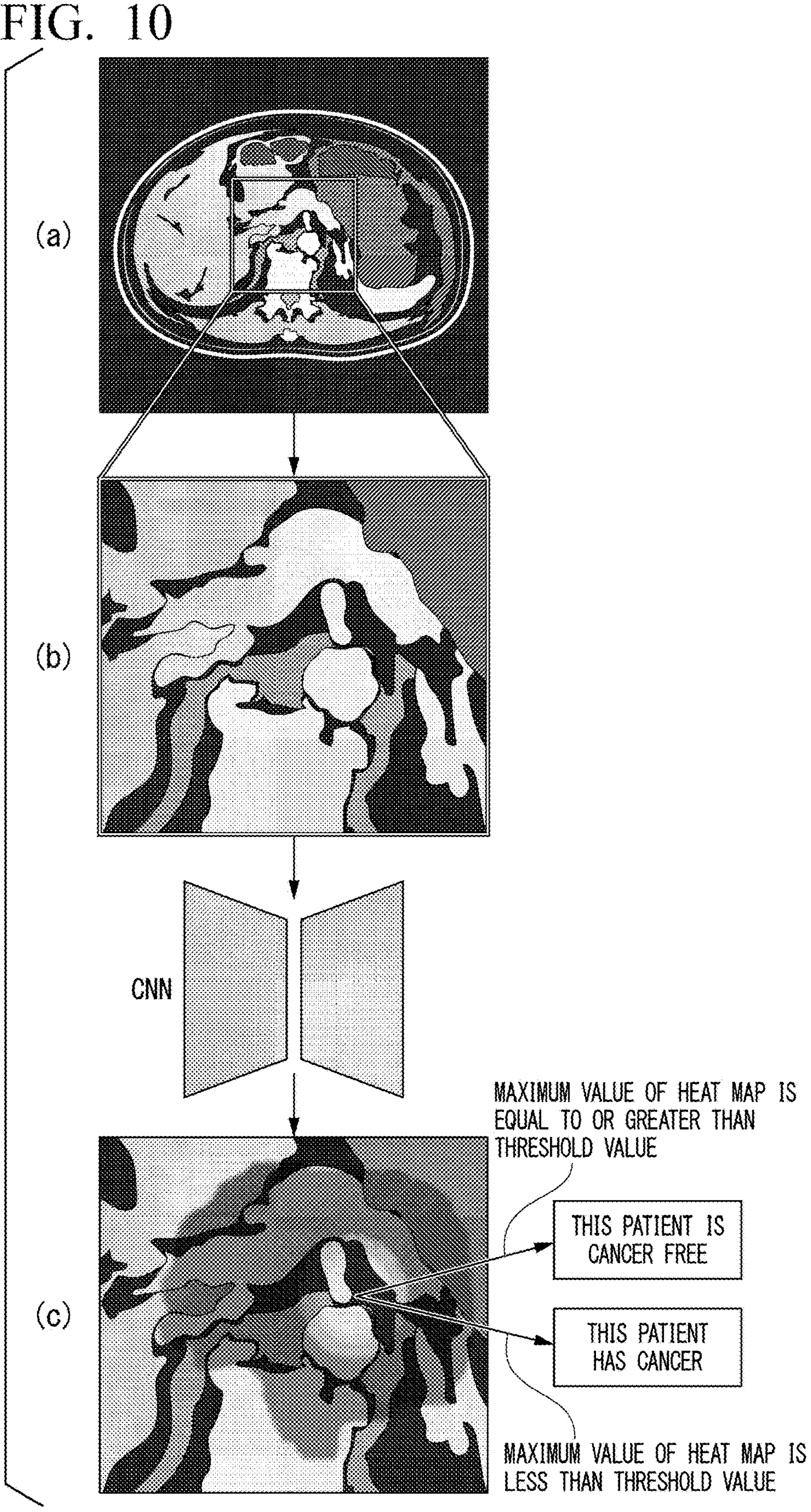
FIG. 10 is a diagram for describing another method of determining the transmittance of a heat map.

Other embodiments will be described below. FIG. 10 is a diagram describing another method of determining the transmittance of a heat map. As illustrated, part of a medical image is cropped (FIG. 10(*a*)) and the cropped part of the image (hereinafter referred to as a cropping image (FIG. 10(*b*))) is input to a trained convolutional neural network (CNN in FIG. 10). The convolutional neural network is a neural network trained on the basis of a training data set in which a heat map adjusted such that the transmittance p of a pixel area where cancer tissues are present decreases is associated with a medical image (or a cropping image cropped from the medical image) of the pancreas of a patient with pancreatic cancer. Accordingly, when the cropping image is input to the trained convolutional neural network, the trained convolutional neural network outputs a heat map in which the transmittance p of an area where cancer tissues are highly likely to exist on the cropping image has been decreased (FIG. 10(*c*)). That is, the trained convolutional neural network outputs a heat map in which cancer tissues are pinpointed and highlighted without being transparent. For example, a medical image of the pancreas of a cancer examination subject (a patient with unknown cancer) is cropped to generate a cropping image. Then, the cropping image derived from the examination subject is input to the trained convolutional neural network. In response to this, the trained convolutional neural network outputs a heat map. For example, if the maximum pixel value on the heat map is equal to or greater than the threshold value, the examination subject can be determined to have a cancer, and if the maximum pixel value on the heat map is less than the threshold value, the examination subject can be determined not to have cancer.

Although several embodiments have been described, these embodiments are presented as examples and are not intended to limit the scope of the invention. These embodiments can be implemented in various other forms, and various omissions, substitutions, and modifications can be made without departing from the spirit of the invention. These embodiments and modifications thereof are included in the scope and spirit of the invention, as well as the scope of the invention described in the claims and equivalents thereof.

What is claimed is:

1. A medical image processing apparatus, comprising:
processing circuitry configured to:
acquire a medical image and a heat map;
determine a transmittance of the heat map based on pixel values of the medical image; and generate a superimposed image that is an image obtained by superimposing the heat map having the determined transmittance on the medical image, wherein the processing circuitry is further configured to
extract a structure or a plurality of structures from the medical image, and
when the plurality of structures, including a first structure and a second structure, are extracted from the medical image, determine the transmittance based on a product of a first weighting factor for the transmittance depending on a pixel value of the medical image, a second weighting factor for the transmittance depending on a distance from a contour of the first structure, and a third weighting factor for the transmittance depending on a distance from a contour of the second structure,
wherein the processing circuitry is further configured to input the medical image into a trained convolutional neural network, and acquire the heat map output by the trained convolutional neural network in response to the input medical image as the heatmap with the determined transmittance, and
the trained convolutional neural network is a neural network trained based on a training data set in which a reference heat map is associated with a reference medical image of a patient, the reference heat map being a heat map adjusted so that the transmittance of a first pixel area containing a lesion is lower than that of a second pixel area not containing the lesion.

2. The medical image processing apparatus according to claim 1, wherein the processing circuitry is further configured to increase the transmittance as a distance from a point of interest increases.

3. The medical image processing apparatus according to claim 1, wherein the processing circuitry is further configured to determine the transmittance based on attributes of a patient who is an imaging target when the medical image is generated.

4. The medical image processing apparatus according to claim 3, wherein the attributes of the patient include an age of the patient, and
the processing circuitry is further configured to increase the transmittance when the patient is older.

5. The medical image processing apparatus according to claim 1, wherein the processing circuitry is further configured to increase the transmittance as the distance from the contour of the first structure decreases.

6. The medical image processing apparatus according to claim 1, wherein the processing circuitry is further configured to cause a display to display the superimposed image.

7. A medical image processing method executed using a computer, the method comprising:

acquiring a medical image and a heat map;

determining a transmittance of the heat map based on pixel values of the medical image;

generating a superimposed image that is an image obtained by superimposing the heat map having the determined transmittance on the medical image;

extracting a structure or a plurality of structures from the medical image; and when the plurality of structures, including a first structure and a second structure, are extracted from the medical image, determining the transmittance based on a product of a first weighting factor for the transmittance depending on a pixel value of the medical image, a second weighting factor for the transmittance depending on a distance from a contour of the first structure, and a third weighting factor for the transmittance depending on a distance from a contour of the second structure, wherein the method further comprises inputting the medical image into a trained convolutional neural network, and acquiring the heat map output by the trained convolutional neural network in response to the input medical image as the heatmap with the determined transmittance, and the trained convolutional neural network is a neural network trained based on a training data set in which a reference heat map is associated with a reference medical image of a patient, the reference heat map being a heat map adjusted so that the transmittance of a first pixel area containing a lesion is lower than that of a second pixel area not containing the lesion.

8. A non-transitory computer-readable storage medium storing a program to be executed by a computer, the program causing the computer to perform a method comprising:

acquiring a medical image and a heat map;

determining a transmittance of the heat map based on pixel values of the medical image;

generating a superimposed image that is an image obtained by superimposing the heat map having the determined transmittance on the medical image;

extracting a structure or a plurality of structures from the medical image; and when the plurality of structures, including a first structure and a second structure, are extracted from the medical image, determining the transmittance based on a product of a first weighting factor for the transmittance depending on a pixel value of the medical image, a second weighting factor for the transmittance depending on a distance from a contour of the first structure, and a third weighting factor for the transmittance depending on a distance from a contour of the second structure, wherein the method further comprises inputting the medical image into a trained convolutional neural network, and acquiring the heat map output by the trained convolutional neural network in response to the input medical image as the heatmap with the determined transmittance, and the trained convolutional neural network is a neural network trained based on a training data set in which a reference heat map is associated with a reference medical image of a patient, the reference heat map being a heat map adjusted so that the transmittance of a first pixel area containing a lesion is lower than that of a second pixel area not containing the lesion.

9. The medical image processing apparatus according to claim 2, wherein the processing circuitry is further configured to set, as the point of interest, a pixel having a largest pixel value on the heat map.

10. The medical image processing apparatus according to claim 1, wherein the processing circuitry is further configured to determine the first weighting factor based on a pixel value of a reference pixel, which is a pixel on the medical image that overlaps with a point of interest on the heat map when the heat map is superimposed on the medical image.

11. The medical image processing apparatus according to claim 10, wherein the first weighting factor corresponding to the pixel value of the reference pixel is smallest, and wherein the first weighting factor corresponding to other pixel values that are smaller or larger than the pixel value of the reference pixel is larger than the first weighting factor corresponding to the pixel value of the reference pixel.

12. The medical image processing apparatus according to claim 1, wherein the processing circuitry is further configured to minimize the second weighting factor corresponding to a pixel value of a reference pixel, which is a pixel on the medical image that overlaps with a point of interest on the heat map when the heat map is superimposed on the medical image, and wherein the processing circuitry is further configured to increase the second weighting factor as the distance from the point of interest increases.

* * * * *